United States Patent [19]

Ghosh et al.

[11] 4,083,841

[45] Apr. 11, 1978

[54] 2,4-DIAMINO-6-METHYL-5-(HALO-PHENYLAZO) PYRIMIDINES

[75] Inventors: Abha Pal Ghosh; Kalyan Kumar Ghosh, both of Raleigh, N.C.

[73] Assignee: Shaw University, Raleigh, N.C.

[21] Appl. No.: 731,542

[22] Filed: Oct. 13, 1976

[51] Int. Cl.$^2$ ............................................ C07C 107/04
[52] U.S. Cl. ..................................... 260/154; 424/226
[58] Field of Search ........................ 260/154, 256.4 N; 424/226

[56] References Cited

U.S. PATENT DOCUMENTS

| | | | |
|---|---|---|---|
| 2,576,939 | 12/1951 | Hitchings et al. | 260/256.4 N |
| 2,579,259 | 12/1951 | Hitchings et al. | 260/256.4 N |
| 2,602,794 | 7/1952 | Hitchings et al. | 260/256.4 N |
| 2,680,740 | 6/1954 | Jacob | 260/256.4 N |

OTHER PUBLICATIONS

Chatterjee et al, *Journal of Medicinal Chemistry,* 1971, vol. 14, No. 12, pp. 1237–1238.
*Merck Index,* Eighth Ed., Merck & Co., Inc.:Rahway, N. J. 1968, "Pyrimethamine", pp. 892–893.
Lythgoe et al., *Chemical Abstracts,* 38:5837$^8$.
Fidler et al., *Chemical Abstracts,* 52:7328g.

*Primary Examiner*—Charles F. Warren
*Attorney, Agent, or Firm*—Holman & Stern

[57] ABSTRACT

Compounds comprising selected 2,4-diamino-6-methyl-5-(halophenylazo) pyrimidines which are highly active as folic acid antagonists. The compounds include 2,4-diamino-6-methyl-5-(m-chlorophenylazo) pyrimidine; 2,4-diamino-6-methyl-5-(p-bromophenylazo) pyrimidine; and 2,4-diamino-6-methyl-5-(p-iodophenylazo) pyrimidine.

4 Claims, No Drawings

2,4-DIAMINO-6-METHYL-5-(HALOPHENYLAZO) PYRIMIDINES

BACKGROUND OF THE INVENTION

This invention relates to pyrimidine derivatives and, more particularly, to a selected group of 2,4-diamino-6-methyl-5-(halophenylazo) pyrimidine compounds having a high level of activity as folic acid antagonists.

Folic acid, which is a naturally occurring compound generally contained in the liver and kidneys, is a required factor for certain metabolic reactions and for the growth of certain microorganisms. Drugs which act to prevent the utilization of folic acid, for example, by a competitive binding action, are known as "folic acid antagonists" or "antifolates." This class of drugs has been successfully used for suppressing immune response and in the treatment of various bacterial diseases, protozoal diseases, neoplastic diseases and psoriasis. Some of the more commonly employed folic acid antagonists include, for example, trimethoprim, which is used either alone or in combination with sulfonamides for various bacterial diseases; pyrimethamine, which is used for the treatment of plasmodial diseases; cycloguanilhydrochloride, which is most frequently primarily considered as an antimalarial agent; aminopterine, which has been used for the treatment of various forms of cancer; and methotrexate, which is used for suppressing immune response, for the treatment of psoriasis, and for various kinds of tumors, particularly for the treatment of cancer in children.

In addition to the above-described folic acid antagonists which have been used clinically, a number of substituted 5-arylazo pyrimidine compounds have previously been investigated for their antifolic activity. One of these compounds, 2,4-diamino-6-methyl-5-(phenylazo) pyrimidine, was involved in a limited study reported by Chatterjee et al (Journal of Medicinal Chemistry, 1971, volume 14, No. 12, pages 1237–1238) to determine the effect of various substituents in the 6-position of the pyrimidine ring of 2,4-diamino-5-(phenylazo) pyrimidine compounds on their inhibitory activity toward dihydrofolate reductase. Chatterjee et al found that introduction of the 6-methyl group resulted in increased activity in comparison with the corresponding 6-unsubstituted and 6-amino compounds, but not to the same extent as did introduction of the 6-hydroxy group. While Chatterjee et al also found that the activity of the 6-hydroxy compound could be further increased by a 6-fold amount by introducing an o-ethyl substituent in the phenyl ring, no similar or any other modification of the 6-methyl compound was reported.

SUMMARY OF THE INVENTION

It is, accordingly, a primary object of the present invention to provide novel compounds having a high level of activity as folic acid antagonists.

Another object of the invention is to provide novel 2,4-diamino-6-methyl-5-(arylazo) pyrimidine compounds having significantly higher levels of folic acid antagonist activity in comparison with the corresponding prior art derivative described above.

The above and other objects are achieved in accordance with the present invention by providing novel 2,4-diamino-6-methyl-5-(halophenylazo) pyrimidine compounds of the formula

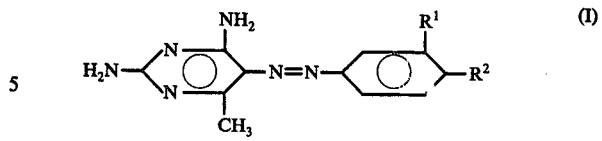

wherein $R^1$ is Cl or H; when $R^1$ is Cl, $R^2$ is H; and when $R^1$ is H, $R^2$ is Br or I. The specific compounds encompassed by Formula I above are 2,4-diamino-6-methyl-5-(m-chlorophenylazo) pyrimidine; 2,4-diamino-6-methyl-5-(p-bromophenylazo) pyrimidine; and 2,4-diamino-6-methyl-5-(p-iodophenylazo) pyrimidine. All three of these compounds are highly active as folic acid antagonists and exhibit significantly higher levels of folic acid antagonist activity in comparison with the prior art 2,4-diamino-6-methyl-5-(phenylazo) pyrimidine.

DESCRIPTION OF PREFERRED EMBODIMENTS

The 2,4-diamino-6-methyl-5-(halophenylazo) pyrimidine compounds in accordance with the present invention are as follows:

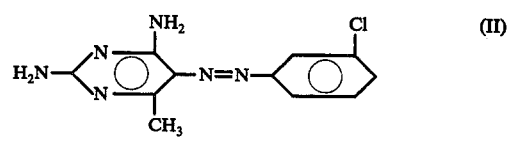

2,4-diamino-6-methyl-5-(m-chlorophenylazo) pyrimidine

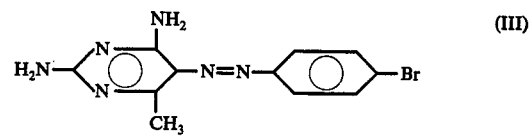

2,4-diamino-6-methyl-5-(p-bromophenylazo) pyrimidine

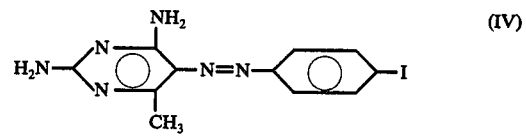

2,4-diamino-6-methyl-5-(p-iodophenylazo) pyrimidine

All three of the above compounds in accordance with the present invention are prepared by coupling of 2,4-diamino-6-methyl pyrimidine with the appropriate diazotized halo aniline, i.e., m-chloro aniline, p-bromo aniline, or p-iodo aniline. The 2,4-diamino-6-methyl pyrimidine, the starting material, may be prepared by a modified procedure of Gabriel and Coleman (Ber., volume 34, page 1253, 1901) by reaction of 2-amino-4-chloro-6-methyl pyrimidine (described by Gabriel and Coleman, Ber., volume 32, page 2924, 1899) with alcoholic ammonia. The coupling reaction is carried out by adding the diazotized halo aniline to a well-cooled and stirred aqueous solution of the 2,4-diamino-6-methyl pyrimidine, and thereafter adjusting the pH of the resulting solution to 7.0, for example, with 30 percent sodium hydroxide solution. The resulting coupled product forms as a precipitate, which is then recovered from the reaction mixture by filtration.

The 2,4-diamino-6-methyl-5-(halophenylazo) pyrimidine compounds in accordance with the present invention all exhibit high levels of activity as folic acid antagonists, as determined by their inhibitory effects upon the growth of the test microorganism *Strep. faecalis* R utilizing folic acid as substrate. The level of antifolic activity exhibited by each of the compounds of the present invention is significantly greater than that exhibited by the prior art 2,4-diamino-6-methyl-5-(phenylazo) pyrimidine, as well as other halophenyl- and alkylphenyl-substituted derivatives of this prior art compound. Moreover, the compounds of the present invention compare quite favorably in their level of antifolic activity with the prior art folic acid antagonists which are presently being used clinically, thereby indicating their utility for the treatment of many of the same conditions by preventing utilization of folic acid.

The invention is further illustrated by way of the following examples.

EXAMPLE I

2,4-Diamino-6-methyl-5-(m-chlorophenylazo) pyrimidine (a) 2,4-Diamino-6-methyl pyrimidine was prepared by a modified procedure of Gabriel and Coleman (Ber., volume 34, page 1253, 1901). A mixture of 2-amino-4-chloro-6-methyl pyrimidine (9.0 gm) and alcoholic ammonia (225 ml), were heated in a steel bomb at 180° C for 6 hours. The mixture was then filtered, and the filtrate was evaporated to dryness. The solid residue was dissolved in 60ml hot water. The solution was cooled to room temperature, and 40 gm of potassium hydroxide was then added. The product thus precipitated, was filtered, and crystallized from acetone, m.p. 183° C. Yield: 5.5gm. U.V. spectrum data corresponded to those reported by Curd and Rose (J.C.S., page 98, 1949).

(b) A solution of 2,4-diamino-6-methyl pyrimidine (1.0 gm) in water (60 ml) was cooled to 0° C in ice-salt bath and stirred mechanically. m-Chloro aniline (1.02 gm) was dissolved in ethanol (10 ml). To this solution 3 N HCl (30 ml) was added and the solution was cooled to −5° C. A solution of sodium nitrite (0.552 gm) in water (5 ml) was also cooled to 0° C. The cold sodium nitrite solution was then added to the cold m-chloro aniline solution. After shaking thoroughly, excess sodium nitrite was decomposed with a trace of urea. The diazotized m-chloro aniline solution was then added to the pyrimidine solution. After stirring for 10 minutes, the pH of the combined solution was adjusted to 7.0 with 30 percent sodium hydroxide solution. A precipitate appeared. After stirring for two hours more, the product was separated by filtration, washed well with water, dried in a vacuum desiccator, and crystallized from ethanol. M.P. 249° C. Yield: 1.65 grams (85 percent).

EXAMPLE II

2,4-Diamino-6-methyl-5-(p-bromophenylazo) pyrimidine

A solution of 2,4-diamino-6-methyl pyrimidine (1.0 gm) in water (60 ml) was cooled to 0° C in ice-salt bath and stirred mechanically. p-Bromo aniline (1.38 gm) was dissolved in ethanol (30 ml) and to this solution 3 N HCl (30 ml) was added. The solution was then allowed to cool to −5° C. A solution of sodium nitrite (0.553 gm) in water (5 ml) was cooled to 0° C. The sodium nitrite solution was then added to the p-bromo aniline solution. After shaking thoroughly, excess sodium nitrite was decomposed with a pinch of urea. The diazotized p-bromo aniline was then added to the pyrimidine solution. After stirring for 10 minutes, the pH of the combined solution was adjusted to 7.0 with 30 percent sodium hydroxide. A precipitate appeared. After stirring for 2 hours more, the product was separated by filtration, dried in vacuum desiccator, and crystallized from butanol. M.P. 245°–46° C. Yield: 2.2 gm (90 percent).

EXAMPLE III

2,4-Diamino-6-methyl-5-(p-iodophenylazo) pyrimidine

A solution of 2,4-diamino-6-methyl pyrimidine (1.0 gm) in water (60 ml) was cooled to 0° C in ice-salt bath and stirred mechanically. p-Iodo aniline (1.84 gm) was dissolved in ethanol (30 ml) and to this solution 3 N HCl (30 ml) was added. The solution was then cooled to −5° C. A solution of sodium nitrite (0.567 gm) in water (5 ml) was also cooled to 0° C. The sodium nitrite solution was then added to the p-iodo aniline solution. After shaking thoroughly, excess sodium nitrite was decomposed with a pinch of urea. The diazotized p-iodo aniline was then added to the pyrimidine solution. After stirring for ten minutes, the pH of the combined solution was adjusted to 7.0 with 30 percent sodium hydroxide. A precipitate appeared. After stirring two hours more, the product was filtered, dried in vacuum desiccator, and crystallized from ethanol. M.P. 243°–44° C. Yield: 2.5 gm (90 percent).

EXAMPLE IV

Each of the three compounds prepared in Examples I, II and III was evaluated for its activity as a folic acid antagonist by determining its inhibitory effect upon the growth of the test microorganism *Strep. faecalis* R (obtained from American Type Culture Collection, catalog No. 8043) utilizing folic acid as substrate. The procedural details of this microbiological assay technique are well known in the art and are described, for example, by Luckey et al (J. Biol. Chem., volume 152, page 157, 1944). Briefly, the test compounds were dissolved in glass-distilled water with the aid of a few drops of hydrochloric acid (2N), and a series of duplicate assay tubes containing graded amounts of the test compound were then prepared. To each of the assay tubes except the blank, folic acid solution was added to give a concentration of 1.5 m$\mu$g/ml of the medium. Water was added to bring the volume to 5 ml. 5 ml of basal medium was then added, the basal medium being the same as the standard folic acid assay medium as recommended by the Association of Vitamin Chemists, Inc., ("Methods of Vitamin Assay," Second Edition, Interscience Pub., New York, 1951), with the modification that all the purines and pyrimidines (viz., adenine, guanine, xanthine and uracil) had been omitted. Each series of the experiments had one blank tube containing basal medium and water only, and standard tubes containing folic acid, water, the same amount of HCl as in the assay tubes, and basal medium only. The assay tubes were then autoclaved at 10 pounds pressure for 10 minutes, and then cooled to room temperature. Each assay tube was then inoculated with one drop of *Strep. faecalis* R inoculum (prepared by standard procedures from the stock culture), shaken well, and incubated at 37° C for 18 hours. Microbial growth was then measured turbidimetrically in a Klett-Summerson photoelectric colorimeter using filter No. 66 (red filter, 640–700 m$\mu$), adjusted so that the uninoculated medium gave a zero reading. A curve was then constructed by plotting the microbial growth as Klett-reading against concentration of the test compound. From the curve, the half-inhibition concentration of the test compound (i.e., the concentration of the test compound at 50 percent of the standard growth) was determined.

The results of these tests carried out with the three compounds in accordance with the present invention are set forth in Table 1, below, with the lowest half-inhibition concentration value indicating the compound with the highest folic acid antagonist activity. For purposes of comparison, Table 1 also includes the results of the same test carried out under the identical conditions with eight other related compounds, including the prior art unsubstituted phenylazo derivative and various other halophenyl-and alkylphenyl-substituted derivatives thereof.

ing different concentrations of folic acid in the assay medium, as indicated in the Table. Reference to the data wherein the folic acid concentration was 0.4 m$\mu$g/ml, is Elslager et al, J. Med. Chem., volume 15, page 827 (1972); while reference to the data wherein the folic acid concentration is 1.0 m$\mu$g/ml, is Chaykovsky et al, J. Med. Chem., volume 17, page 1212 (1974).

TABLE II

| COMPOUND | Folic Acid Concentration m$\mu$g/ml | Half-Inhibition Concentration, $\mu$g/ml |
|---|---|---|
| Trimethoprim | 0.4 | 0.012 |
| Pyrimethamine | 0.4 | 0.004 |
| Cycloguanil hydrochloride | 0.4 | 0.008 |
| Aminopterin | 0.4 | 0.002 |
| Methotrexate | 0.4 | 0.0002 |
| Methotrexate | 1.0 | 0.002 |

It should first of all be noted that the half-inhibition concentration values obtained in these tests for any given compound will vary with the concentration of folic acid employed in the assay medium, the higher the folic acid concentration, the higher the half-inhibition concentration value that will be obtained. This is shown from a comparison of the last two entries in Table II, where a 2.5-fold increase in the folic acid concentration in the assay medium resulted in a 10-fold increase in the half-inhibition concentration value obtained for metho-

TABLE I

| COMPOUND | Half-Inhibition Concentration, $\mu$g/ml |
|---|---|
| 2,4-diamino-6-methyl-5-(m-chlorophenylazo) pyrimidine | 0.003 |
| 2,4-diamino-6-methyl-5-(p-bromophenylazo) pyrimidine | 0.004 |
| 2,4-diamino-6-methyl-5-(p-iodophenylazo) pyrimidine | 0.0021 |
| 2,4-diamino-6-methyl-5-(phenylazo) pyrimidine | 0.0075 |
| 2,4-diamino-6-methyl-5-(o-ethylphenylazo) pyrimidine | 0.0068 |
| 2,4-diamino-6-methyl-5-(p-ethylphenylazo) pyrimidine | 0.026 |
| 2,4-diamino-6-methyl-5-(p-chlorophenylazo) pyrimidine | 0.0062 |
| 2,4-diamino-6-methyl-5-(p-fluorophenylazo) pyrimidine | 0.009 |
| 2,4-diamino-6-methyl-5-(o-fluorophenylazo) pyrimidine | 0.038 |
| 2,4-diamino-6-methyl-5-(o-chlorophenylazo) pyrimidine | 0.023 |
| 2,4-diamino-6-methyl-5-(o-bromophenylazo) pyrimidine | 0.011 |

As can be seen from the data of Table I, all three of the compounds of the present invention exhibited a substantially higher level of folic acid antagonist activity in comparison with the prior art unsubstituted phenyl derivative, ranging from an almost 2-fold increase in activity for the p-bromophenyl derivative to a greater than 3.5-fold increase in activity for the p-iodophenyl derivative. On the other substituted phenyl derivatives tested, only the p-chlorophenyl and o-ethylphenyl derivatives exhibited even a slight increase in activity in comparison with the unsubstituted phenyl derivative, but not nearly to the same extent as the three compounds of the present invention. All of the other substituted phenyl derivatives tested exhibited lower levels of activity than the unsubstituted phenyl derivative. In all cases, the inhibitory action is competitive and the incorporation into the assay medium of excess folic acid, 5-formyl-tetrahydrofolic acid and thymine resulted in a complete reversal of the growth-inhibitory effects of the test compounds.

EXAMPLE V

For purposes of further comparison with the compounds of the present invention, the folic acid antagonist activity data for each of the five known clinically used and commercially available antifolate compounds described above, are set forth in Table II, below. These data were obtained against the test microorganism Strep. faecalis R by means of the same microbiological assay technique described in Example IV, but employtrexate. It is thus evident that if the folic acid concentration in the assay medium had been 1.5 m$\mu$g/ml, as in Example IV, above, the half-inhibition concentration values for the compounds listed in Table II would have been substantially higher than those reported. With this in mind, a comparison of the data of Table II with that set forth in Table I for the three compounds in accordance with the present invention, indicates that the level of folic acid antagonist activity exhibited by the compounds of the present invention compares quite favorably with that exhibited by the known clinically used and commercially available antifolate compounds.

The embodiments of the invention in which an exclusive property or privilege is claimed are defined as follows:

1. A 2,4-diamino-6-methyl-5-(halophenylazo) pyrimidine compound of the formula

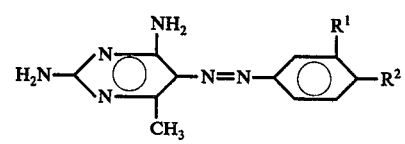

wherein R$^1$ is Cl or H; when R$^1$ is Cl, R$^2$ is H; and when R$^1$ is H, R$^2$ is Br or I.

2. The compound according to claim 1, which is 2,4-diamino-6-methyl-5-(m-chlorophenylazo) pyrimidine.

3. The compound according to claim 1, which is 2,4-diamino-6-methyl-5-(p-bromophenylazo) pyrimidine.

4. The compound according to claim 1, which is 2,4-diamino-6-methyl-5-(p-iodophenylazo) pyrimidine.